United States Patent [19]

Trick

[11] 4,386,601
[45] Jun. 7, 1983

[54] ARTIFICIAL SPHINCTER

[75] Inventor: Robert E. Trick, Racine, Wis.

[73] Assignee: Medical Engineering Corporation, Racine, Wis.

[21] Appl. No.: 292,051

[22] Filed: Aug. 12, 1981

[51] Int. Cl.³ ............................................. A61B 17/00
[52] U.S. Cl. .................................... 128/1 R; 128/346; 128/DIG. 25
[58] Field of Search ........ 128/1 R, 325, 346, DIG. 25; 138/30; 3/1

[56] References Cited

U.S. PATENT DOCUMENTS

| | | | |
|---|---|---|---|
| 4,056,095 | 11/1977 | Rey et al. | 128/1 R |
| 4,152,786 | 5/1979 | Clark et al. | 138/30 X |
| 4,167,201 | 9/1979 | Zahid | 128/30 |
| 4,210,132 | 7/1980 | Perlin | 128/1 R |
| 4,222,377 | 9/1980 | Burton | 128/1 R |
| 4,335,751 | 6/1982 | Sagimura et al. | 138/30 |

OTHER PUBLICATIONS

Kintzonidis et al.-Trans. Amer. Soc. Art. Inter. Orgs., vol. XVII, 1971, pp. 138-142.

Primary Examiner—Dalton L. Truluck
Attorney, Agent, or Firm—Quarles & Brady

[57] ABSTRACT

An artificial sphincter comprises an inflatable occlusion means which is normally inflated with hydraulic fluid under pressure to cut off flow through a body passage, an improved accumulator balloon having a relatively inelastic shell which serves as a reservoir for hydraulic fluid for the inflatable occlusion means and a gas filled bladder which controls fluid pressure in the closed system, a pump to suck fluid from the occlusion means to deflate it and open the body passage to fluid flow and tubing connecting the inflatable occlusion means, the accumulator balloon and the pump to form a closed system. The sphincter also includes a first check valve at the inflatable occlusion means which allows fluid to freely flow out of the inflatable occlusion means, a second check valve at the accumulator balloon which allows fluid to freely flow into the accumulator balloon and resistance means which restricts fluid flow into the inflatable occlusion means and out of the accumulator balloon to a low rate of flow.

4 Claims, 4 Drawing Figures

4,386,601

ARTIFICIAL SPHINCTER

The present invention relates to an improved artificial sphincter for reversibly closing a body passage.

BACKGROUND OF THE INVENTION

Many persons have non-functioning or malfunctioning sphincters which because of congenital malformations, trauma to the sphincter nerves or muscles, or disease of the sphincter nerves or muscles make it impossible for them to control the discharge of body waste.

One of the most troublesome and embarrassing conditions is the malfunctioning of the urethral sphincter. The urethral sphincter retains urine in the bladder until the sphincter is relaxed which permits the urine to be discharged. As a result of the malfunctioning of the urethral sphincter, uncontrolled drainage of urine from the body can occur. Obviously, this can be embarrassing to the individual and can restrict his activities.

Attempts have been made in the past to provide an artificial sphincter which can serve as a substitute for a malfunctioning urethral sphincter or provide means for controlling artificial openings that have no natural sphincters.

None of the prior art attempts have been completely successful. Therefore, a need still exists for an improved artificial sphincter for reversibly closing body passages.

SUMMARY OF THE INVENTION

It is an object of the present invention to provide a novel artificial sphincter for efficiently and reversibly closing a body passage.

It is a further object of the present invention to provide an implantable artificial sphincter with an improved accumulator balloon.

The artificial sphincter of the present invention comprises a closed hydraulic system which includes an inflatable occlusion means which is normally inflated with hydraulic fluid under pressure to cut off flow through a body passage, an improved accumulator balloon having a relatively inelastic shell which serves as a reservoir for hydraulic fluid for the inflatable occlusion means and a gas filled bladder which controls fluid pressure in the closed system, a pump to suck fluid from the occlusion means to deflate it and open the body passage to fluid flow and tubing connecting the inflatable occlusion means, the accumulator balloon and the pump to form a closed system. The sphincter also includes a first check valve at the inflatable occlusion means which allows fluid to freely flow out of the inflatable occlusion means, a second check valve at the accumulator balloon which allows fluid to freely flow into the accumulator balloon and resistance means which restricts fluid flow into the inflatable occlusion means and out of the accumulator balloon to a low rate of flow.

In one embodiment of the apparatus, the inflatable occlusion means is an inflatable cuff which can be positioned about the outside of a flexible wall of a body passage. The cuff when inflated collapses the wall and stops flow through the body passage. In another embodiment, the inflatable occlusion means is a balloon which is adapted to be positioned in a body passage. The balloon when inflated occludes the lumen of the body passage and thus stops flow.

BRIEF DESCRIPTION OF THE DRAWINGS

The invention will be hereinafter more fully described with reference to the accompanying drawings in which.

DESCRIPTION OF THE PREFERRED EMBODIMENT

Figure 1:
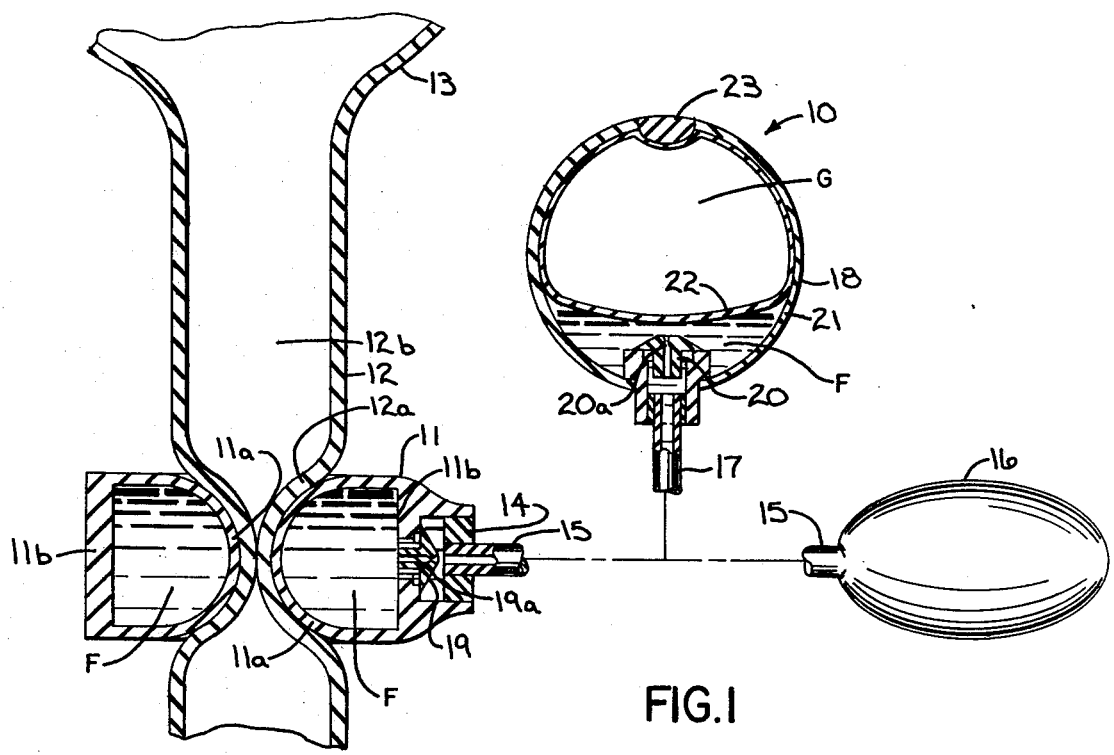
FIG. 1 is a view, partly in section, of one embodiment of the artificial sphincter of the present invention with the body passage closed.
Figure 2:
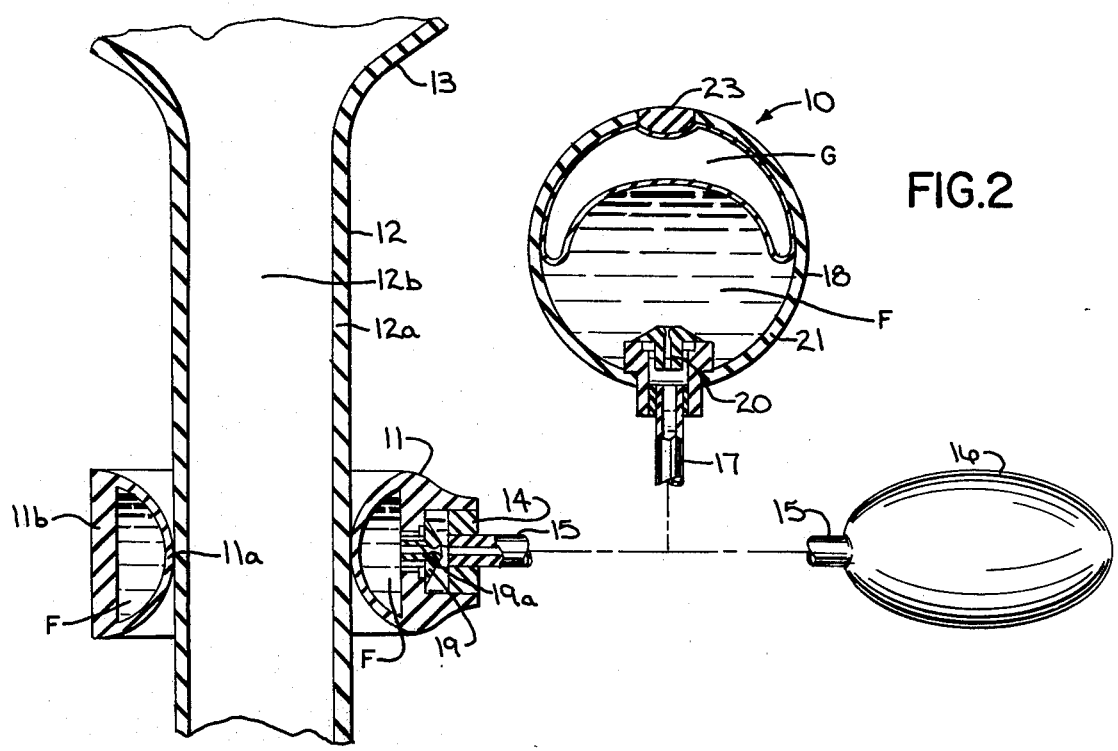
FIG. 2 is a view similar to FIG. 1 with the body passage open.

The preferred embodiment of the artificial sphincter of the present invention seen in FIGS. 1 and 2 is generally designated 10. As seen therein an inflatable cuff 11 of the sphincter 10 is positioned about an urethra 12 leading from a bladder 13. The natural urethra normally is opened or closed by one or more sphincters (not shown) which are controlled by voluntary nerve impulses. The words "bladder" and "urethra" as used herein are intended to include both the natural or artificial bladder and urethra or any other suitable natural or artificial structures which perform similar body functions.

Still referring to FIGS. 1 and 2, it can be seen that the inflatable cuff 11 has a port 14 which is connected by a tubing 15 to a pump 16. A branch 17 in the tubing 15 leads to an accumulator balloon 18. Both the cuff 11 and the accumulator balloon 18 are equipped with combination check/resistance valves 19 and 20, respectively. The valve 19 allows the free flow of fluid out of the cuff 11 and restricts flow into the cuff 11 to a low rate of flow. The check/resistance valve 20 allows the free flow of fluid into the accumulator balloon 18 and resists flow out to a low rate of flow.

As seen in the drawings, the accumulator balloon 18 has a relatively thick inelastic shell 21 which contains a closed gas filled bladder 22 provided with a resealable valve or septum 23 through which gas can be added or removed from the bladder 22 with a hollow needle (not shown).

In the embodiment shown in FIGS. 1 and 2, the actual closing and opening of the urethra 12 is accomplished by inflating the cuff 11 to collapse the wall 12a of the urethra 12 and close the lumen 12b (as seen in FIG. 1). Although the cuff 11 is inflatable, it does not have to be elastic as the term is normally understood. However, it is necessary that the cuff 11 have a readily deformable inner wall 11a. The deformable wall 11a is preferably thinner and thus more elastic and deformable than the outer wall 11b. However, it will be appreciated that the difference in deformability of the walls 11a and 11b can be achieved by other techniques than varying the thickness, e.g. making 11b of a less flexible or elastic material.

The operation of the artificial sphincter 10 which controls the flow of fluid through the urethra 12 now will be described in connection with FIGS. 1 and 2.

The cuff 11 is normally inflated as seen in FIG. 1 causing the wall 12a of the urethra 12 to be collapsed closing the lumen 12b. When it desired to empty the bladder 13, the cuff 11 is deflated to permit the natural resiliency of the wall 12a of the urethra to cause the lumen 12b to open. The cuff 11 is normally inflated and it can be deflated by repeatedly stroking the pump 16 to suck fluid F out of the cuff 11. As the cuff 11 is rapidly emptied of fluid it deflates and the lumen 12b of the urethra opens. When the pump 16 is stroked the fluid sucked from the cuff 11 is forced by the pump 16 via the tubing 15 and 17 into the shell 21 of the accumulator balloon 18. As the shell 21 of the accumulator balloon 18 fills with fluid, the gas G in the bladder 22 is compressed to occupy less space within the shell 21 to accommodate the additional fluid from the cuff 11 and pump 16. When the cuff 11 is fully open the bladder 22 and accumulator balloon 18 are in the state seen in FIG. 2. The refilling or reinflation of the cuff 11 which commences immediately when the pump 16 is not stroked is delayed by the resistance means, i.e. openings 19a and 20a of valves 19 and 20. The resistance openings 19a and 20a, which could be replaced if desired by a single resistance member, allow the fluid to only slowly leak back into the cuff 11 at a low rate of flow. During the slowed refilling the bladder 13 is emptied. The refilling of the cuff 11 is automatic once the squeezing of the pump 16 has stopped because the gas in bladder 22 which has been compressed by the fluid F forced into the shell 21 by the pump 16 starts to expand to its maximum size. As the bladder 22 expands, the fluid in the shell 21 leaks through the resistance openings 20a and passes via the tubing 17 and 15 and the resistance opening 19a into the cuff 11 causing it to reinflate and close the lumen 12b.

The improved accumulator balloon 18 with its inelastic, preferably relatively thick, shell 21 and its gas filled bladder 22 provides more constant pressure and is longer lasting than the prior art accumulating devices which were usually simple elastic silicone balloons. Such balloons depended upon their wall thickness and the quantity of fluid they contained to maintain pressure within desired ranges. After extended use such silicone balloons tended to take a set causing pressure control to degrade and necessitating replacement of the system. The shell 21 of the accumulator balloon 18 preferably has sufficient wall thickness to render it inelastic under conditions of use and to eliminate any set of the silicone and the gas filled bladder 22 establishes the working pressure of the accumulator balloon 18. The bladder 22 is made of an elastomer which does not allow the gas to diffuse into the fluid and it is sized and shaped so that it is under negligible stress and no pressure differential exists between the gas and fluid. The gas pressure in the bladder 22 can be adjusted by penetrating the septum 23 with a hollow needle (not shown) to add or remove gas. As seen in FIG. 1 the bladder 22 has attained maximum size with negligible stress in the walls and most of the fluid is in the cuff 11.

Figure 3:
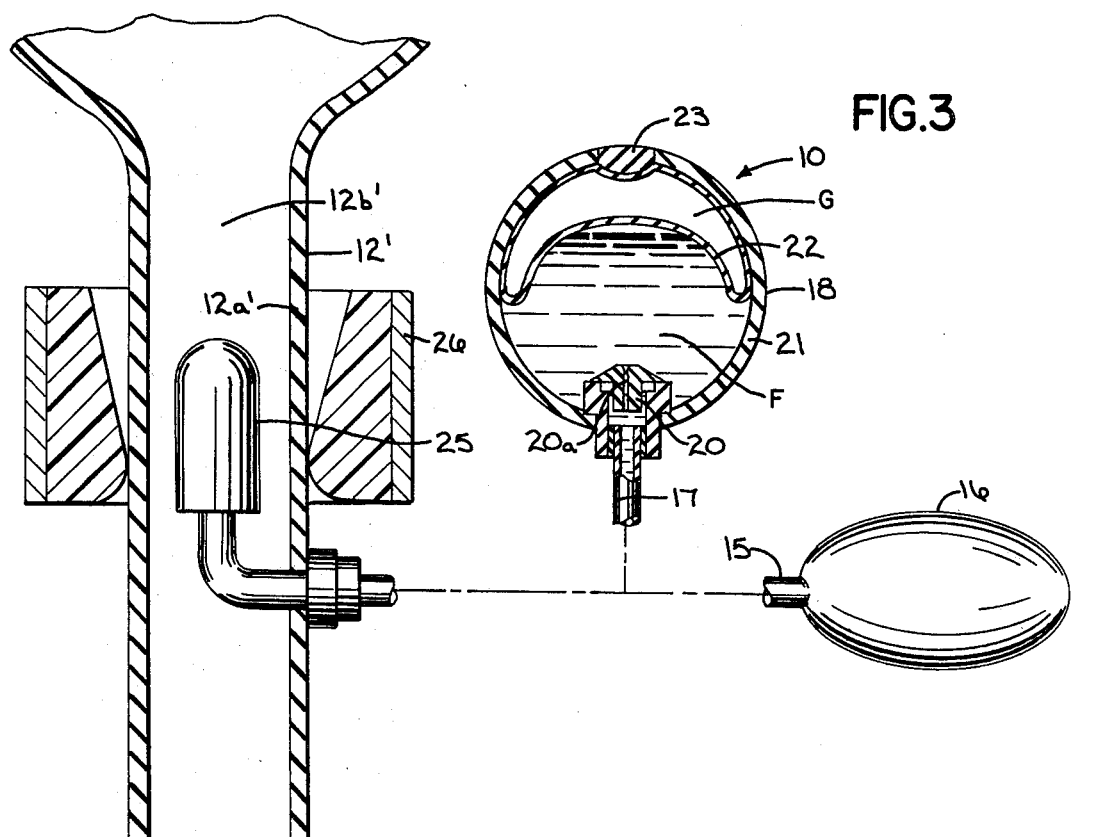
FIG. 3 is a view similar to FIG. 2 but of a second embodiment of the artificial sphincter of the present invention with the body passage open.
Figure 4:
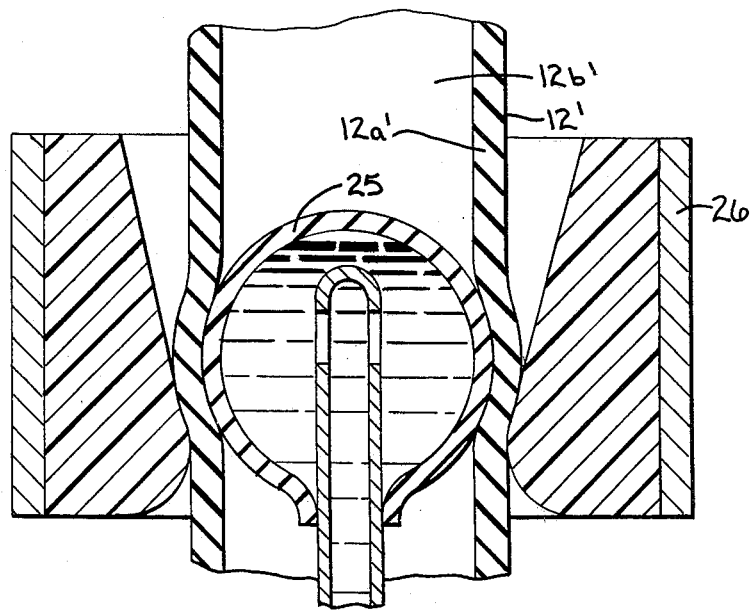
FIG. 4 is an enlarged partial view of the embodiment of FIG. 3 showing the occlusion means inflated and the body passage closed.

The second embodiment of the artificial sphincter of the present invention is seen in FIGS. 3 and 4. As seen therein, the second embodiment differs from the embodiment of FIGS. 1 and 2 primarily in that the inflatable occlusion means used to close the body passage, instead of being a cuff, is a balloon 25 which is positioned within the lumen 12b' of the urethra 12'. Although the balloon 25 can be used by itself to occlude the lumen 12b', it is preferably used in conjunction with a relatively rigid tapered collar or seat 26 as seen best in FIG. 4. The seat 26 which is positioned about the outside wall of the urethra 12' serves to prevent the flexible urethra wall 12a' from being expanded or stretched and potentially damaged by the over inflation of the balloon 25.

Prior to implanting either of the described embodiments, the closed systems are initially filled with hydraulic fluid under a slight pressure. The fluid preferred for this purpose is of physiological saline. Other hydraulic fluids can be used but should be physiologically compatible with body tissue and body organs in the event that a leak would develop in the system. Adjustments in the fluid contents can be made through an addible on the pump bulb (not shown).

The components of the sphincter of the present invention are preferably made of medical grade polymer such as silicone rubber, and the fluid-tight connections between the various components are preferably made with an implantable grade of silicone adhesive of which several types are commercially available.

The apparatus of the present invention preferably is implanted completely within the patient's body. This may be done by making a suitable incision through the skin so as to provide access to the abdominal cavity. With the abdominal cavity opened, the urethra can be exposed and the cuff or balloon properly positioned. The pump which may take other form than the pressure bulb shown should be arranged where it can be operated from the outside and the abdominal cavity surgically closed. The manner of the implantation described is generic for both males and females. The systems disclosed are sufficiently versatile to allow implanting in various regions of the body. For example, for male patients it may be preferable to implant the pump in the patient's scrotum.

It will be appreciated by those skilled in the art that the foregoing description of the preferred embodiments for use in controlling the urethra has been for purposes of illustration only as the apparatus and the method of the present invention can be used to control flow through other body passages such as the colon. In addition, it is to be understood that the novel accumulator balloon may be used in other implantable systems such as penile prosthesis. Therefore, it is intended that the scope of the invention not be limited except by the claims which follow.

I claim:

1. An artificial sphincter for controlling the flow of fluid through a body passage which comprises a closed system which includes:
   (a) an inflatable occlusion means which is normally inflated with hydraulic fluid to close the body passage;
   (b) an improved accumulator including a rigid inelastic shell which serves as a reservoir for hydraulic fluid and a gas filled bladder disposed within said shell, said bladder having a resealable means which permits gas to be introduced into or removed from the bladder with a hollow needle thereby permitting the fluid pressure in closed system to be adjusted without opening said system;
   (c) pump means for sucking hydraulic fluid from the inflatable occlusion means causing it to deflate and the body passage to open;
   (d) tubing connecting the pump means to the inflatable occlusion means and the pump means to the accumulator balloon to form a closed system;
   (e) valve means allowing free flow out of the inflatable occlusion means and into the accumulator reservoir; and (f) resistance means fluidly interposed between said occlusion means and said accumulator which allows fluid to flow at a low rate into the inflatable occlusion means and out of the accumulator.

2. The sphincter of claim 1 in which the inflatable occlusion means is a cuff.

3. The sphincter of claim 1 in which the inflatable occlusion means is a balloon.

4. An artificial sphincter for controlling the flow of fluid through a body passage which comprises a closed system which includes:
   (a) an inflatable occlusion means which is normally inflated with hydraulic fluid to close the body passage;
   (b) an improved accumulator including a rigid inelastic shell which serves as a reservoir for hydraulic fluid and a gas filled bladder disposed within said shell for controlling fluid pressure in the closed system, said bladder having a resealable means which permits gas to be introduced into or removed from the bladder with a hollow needle without opening said closed system;
   (c) pump means for sucking hydraulic fluid from the inflatable occlusion means causing it to deflate and the body passage to open;
   (d) tubing connecting the pump means to the inflatable occlusion means and the pump means to the accumulator balloon to form a closed system;
   (e) valve means allowing free flow out of the inflatable occlusion means and into the accumulator reservoir; and
   (f) a flow restrictor means taking the form of a reduced diameter opening into said valve means so as to be fluidly connected intermediate to said occlusion means and said gas filled bladder for reducing the flow of fluid into said occlusion means and out of said gas filled bladder.

* * * * *